(12) United States Patent
Sun et al.

(10) Patent No.: US 10,706,550 B2
(45) Date of Patent: Jul. 7, 2020

(54) SYSTEM AND METHOD FOR POSITRON EMISSION TOMOGRAPHY IMAGING

(71) Applicant: SHANGHAI UNITED IMAGING HEALTHCARE CO., LTD., Shanghai (CN)

(72) Inventors: Youjun Sun, Shanghai (CN); Xiaoyue Gu, Shanghai (CN); Weiping Liu, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 221 days.

(21) Appl. No.: 15/984,542

(22) Filed: May 21, 2018

(65) Prior Publication Data
US 2018/0350078 A1    Dec. 6, 2018

(30) Foreign Application Priority Data

May 25, 2017   (CN) .......................... 2017 1 0380869

(51) Int. Cl.
| | | |
|---|---|---|
| *G06T 11/00* | (2006.01) | |
| *A61B 6/03* | (2006.01) | |
| *G06T 7/11* | (2017.01) | |
| *G06T 7/00* | (2017.01) | |
| *G06T 7/13* | (2017.01) | |
| *A61B 6/00* | (2006.01) | |
| *G06T 7/33* | (2017.01) | |

(52) U.S. Cl.
CPC ................ *G06T 7/11* (2017.01); *A61B 6/032* (2013.01); *A61B 6/037* (2013.01); *A61B 6/488* (2013.01); *A61B 6/5205* (2013.01); *A61B 6/5211* (2013.01); *A61B 6/5235* (2013.01); *A61B 6/545* (2013.01); *G06T 7/0012* (2013.01); *G06T 7/13* (2017.01); *G06T 7/33* (2017.01); *G06T 11/003* (2013.01); *G06T 11/006* (2013.01); *A61B 6/4417* (2013.01); *G06T 2200/04* (2013.01); *G06T 2207/10081* (2013.01); *G06T 2207/10104* (2013.01)

(58) Field of Classification Search
CPC ... G06T 7/0012; G06T 11/003; G06T 11/006; G06T 2207/10081; G06T 2207/10084; G06T 2207/10104; G06T 2207/20212; G06T 2207/20221; A61B 6/032; A61B 6/037; A61B 6/4417; A61B 6/488; A61B 6/5205; A61B 6/5229; A61B 6/5235
See application file for complete search history.

(56) References Cited

U.S. PATENT DOCUMENTS

| | | | | |
|---|---|---|---|---|
| 2008/0273780 | A1* | 11/2008 | Kohlmyer et al. | .... A61B 6/032 382/131 |
| 2012/0078089 | A1* | 3/2012 | Wollenweber et al. | ...................... A61B 6/032 600/427 |

(Continued)

*Primary Examiner* — Andrew W Johns
(74) *Attorney, Agent, or Firm* — Metis IP LLC

(57) ABSTRACT

Systems and methods for image reconstruction are provided. The methods may include obtaining a scout image including a target object, determining a first area and a second area based on the scout image, wherein the second area is located in the first area, obtaining positron emission tomography (PET) data of the first area and first computed tomography (CT) data of the second area, and reconstructing a PET image with respect to the first area based on the PET data and the first CT data.

20 Claims, 12 Drawing Sheets

(56) References Cited

U.S. PATENT DOCUMENTS

2014/0148684 A1* 5/2014 Foo et al. .............. A61B 6/037
 600/411
2017/0164911 A1* 6/2017 Lv et al. ................ A61B 6/037

* cited by examiner

SYSTEM AND METHOD FOR POSITRON EMISSION TOMOGRAPHY IMAGING

CROSS-REFERENCE TO RELATED APPLICATIONS

This application claims priority to Chinese Patent Application No. 201710380869.7, filed on May 25, 2017, the contents of which are incorporated herein by reference.

TECHNICAL FIELD

The present disclosure generally relates to medical imaging, and more particularly to a system and method for positron emission tomography (PET)-computed tomography (CT) imaging.

BACKGROUND

Nuclear medicine tomographic imaging techniques, such as positron emission tomography (PET), computed tomography (CT), use radiation to produce images of a patient. During a PET-CT imaging process, CT data and PET data may be obtained to produce a PET image. Traditionally, both CT data and PET data may be acquired from one area, which may increase radiation exposure of a patient. Thus, there is a need for a system and method for reducing radiation exposure as well as improving image quality.

SUMMARY

In an aspect of the present disclosure, a method implemented on a computing device having at least one processor and a storage device is provided. The method may include obtaining, by the at least one processor, a scout image including a target object. The method may also include determining, by the at least one processor, a first area and a second area based on the scout image, wherein the second area is located in the first area. The method may further include obtaining, by the at least one processor, Positron Emission Tomography (PET) data of the first area and first Computed Tomography (CT) data of the second area. The method may still further include reconstructing, by the at least one processor, a PET image with respect to the first area based on the PET data and the first CT data.

In another aspect of the present disclosure, a system for reconstructing PET images is provided. The system may include a storage device including a set of instructions. The system may also include at least one processor configured to communicate with the storage device. When executing the set of instructions, the at least one processor may cause the system to perform one or more of the following operations. The at least one processor may be configured to cause the system to obtain a scout image including a target object. The at least one processor may be configured to cause the system to determine a first area and a second area based on the scout image, wherein the second area is located in the first area. The at least one processor may be configured to cause the system to obtain Positron Emission Tomography (PET) data of the first area and first Computed Tomography (CT) data of the second area. The at least one processor may be configured to cause the system to reconstruct a PET image with respect to the first area based on the PET data and the first CT data.

In yet another aspect of the present disclosure, a non-transitory computer readable medium is provided. The non-transitory computer readable medium storing instructions, the instructions, when executed by a computing device, may cause the computing device to perform one or more of the following operations. The operations may include obtaining, by the at least one processor, a scout image including a target object. The operations may also include determining, by the at least one processor, a first area and a second area based on the scout image, wherein the second area is located in the first area. The operations may further include obtaining, by the at least one processor, Positron Emission Tomography (PET) data of the first area and first Computed Tomography (CT) data of the second area. The operations may still further include reconstructing, by the at least one processor, a PET image with respect to the first area based on the PET data and the first CT data.

In an aspect of the present disclosure, a method implemented on a computing device having at least one processor and a storage device is provided. The method may include obtaining, by the at least one processor, a scout image including a target object. The method may also include determining, by the at least one processor, a first area based on the scout image. The method may further include adjusting, by the at least one processor, the first area to the center of a Positron Emission Tomography (PET) scanning field-of-view (FOV). The method may still further include obtaining, by the at least one processor, PET data and attenuation information of the first area. The method may still further include reconstructing, by the at least one processor, a PET image with respect to the first area based on the PET data and the first CT data.

In some embodiments, the method may further include determining whether the scout image includes a non-target object and determining the first area based on a result of the determination as to whether the scout image includes a non-target object.

In some embodiments, the method may further include designating a scan area corresponding to the scout image as the first area, according to a result of the determination that the scout image does not include a non-target object.

In some embodiments, the method may further include according to a result of the determination that the scout image includes a non-target object, obtaining a pre-scan area based on the scout image, and determining the first area by extending the pre-scan area to a first boundary.

In some embodiments, the method may further include determining an edge of the non-target object and determining the first boundary according to the edge of the non-target object.

In some embodiments, the method may further include obtaining a pre-scan area based on the scout image. The method may further include determining whether the target object is included in the pre-scan area. The method may further include determining the second area based on a result of the determination as to whether the target object is included in the pre-scan area.

In some embodiments, the method may further include designating the pre-scan area as the second area, according to a result of the determination that the target object is included in the pre-scan area.

In some embodiments, the method may further include determining the second area by extending the pre-scan area to a second boundary, according to a result of the determination that the target object is not included in the pre-scan area.

In some embodiments, the method may further include determining an edge of the target object and determining the second boundary according to the edge of the target object.

In some embodiments, the method may further include obtaining second CT data of the first area without a target object.

In some embodiments, the method may further include determining a third area based on the scout image, the third area being located in the first area and differing from the second area. The method may further include obtaining attenuation information of the third area. The method may further include reconstructing the PET image with respect to the first area based on the PET data, the first CT data, and the attenuation information of the third area.

In some embodiments, the method may further include obtaining attenuation information of a scanning table and air in the third area.

In some embodiments, the scout image is a CT image or an optical image.

In some embodiments, the method may further include obtaining a sensitivity distribution of a PET scanning field-of-view (FOV) and determining the first area based on the scout Image and the sensitivity distribution.

In some embodiments, the method may further include determining a center of the first area. The method may further include determining a first location in the PET scanning FOV based on the sensitivity distribution. The method may further include adjusting the center of the first area to the first location.

In some embodiments, the method may further include determining a center of a PET scanning field-of-view (FOV). The method may further include adjusting the first area to the center of the PET scanning FOV.

In another aspect of the present disclosure, a system for reconstructing PET images is provided. The system may include an image acquisition module, area determination unit, reconstruction data acquisition unit and reconstruction unit. The image acquisition module may be configured to obtain a scout image including a target object. The area determination unit may be configured to determine a first area and a second area based on the scout image, wherein the second area is located in the first area. Reconstruction data acquisition unit may be configured to obtain Positron Emission Tomography (PET) data of the first area and first Computed Tomography (CT) data of the second area. Reconstruction unit may be configured to reconstruct a PET image with respect to the first area based on the PET data and the first CT data.

In a further aspect of the present disclosure, a non-transitory computer readable medium is provided. The non-transitory computer readable medium storing instructions, the instructions, when executed by a computer, may cause the computer to implement a method. The method may include one or more of the following operations. The operations may include obtaining, by the at least one processor, a scout image including a target object. The operations may also include determining, by the at least one processor, a first area and a second area based on the scout image, wherein the second area is located in the first area. The operations may further include obtaining, by the at least one processor, Positron Emission Tomography (PET) data of the first area and first Computed Tomography (CT) data of the second area. The operations may still further include reconstructing, by the at least one processor, a PET image with respect to the first area based on the PET data and the first CT data.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
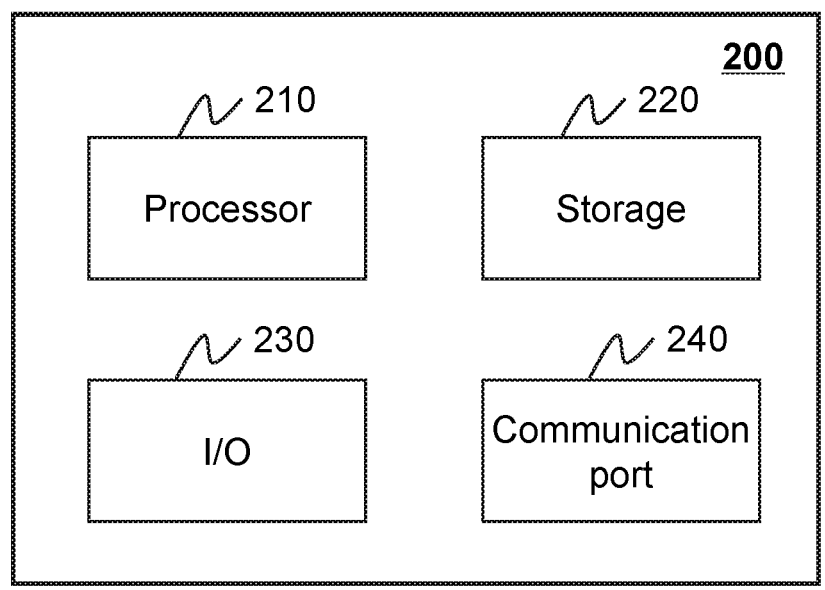
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging, such as for disease diagnosis or research purposes. In some embodiments, the imaging system may be a computed tomography (CT) system, a positron emission tomography (PET) system, an emission computed tomography (ECT) system, a magnetic resonance imaging (MRI) system, an ultrasonography system, an X-ray photography system, or the like, or any combination thereof.

For illustration purposes, the present disclosure is directed to systems and methods for producing a PET image of a target object in a first area (i.e., PET imaging area). The first area may include a second area encompassing the target object and a third area without the target object. The system may reconstruct the PET image based on PET data associated with the first area and CT data associated with the first area, which includes CT data associated with the second area (also referred to herein as "first CT data") and CT data associated with the third area (also referred to herein as "second CT data"). The first CT data may be obtained by scanning the second area including the target object. The second CT data may be obtained by scanning the third area before or after a target object is scanned.

The following descriptions are provided to help better understanding PET image reconstruction methods and/or systems. Merely for illustration purposes, the term "reconstruction data" used in this disclosure may refer to PET data, CT data, PET data, and CT data, or projection data corresponding to the PET/CT data. This is not intended to limit the scope the present disclosure. For persons having ordinary skills in the art, a certain amount of variations, changes, and/or modifications may be deducted under the guidance of the present disclosure. Those variations, changes, and/or modifications do not depart from the scope of the present disclosure.

Figure 1:
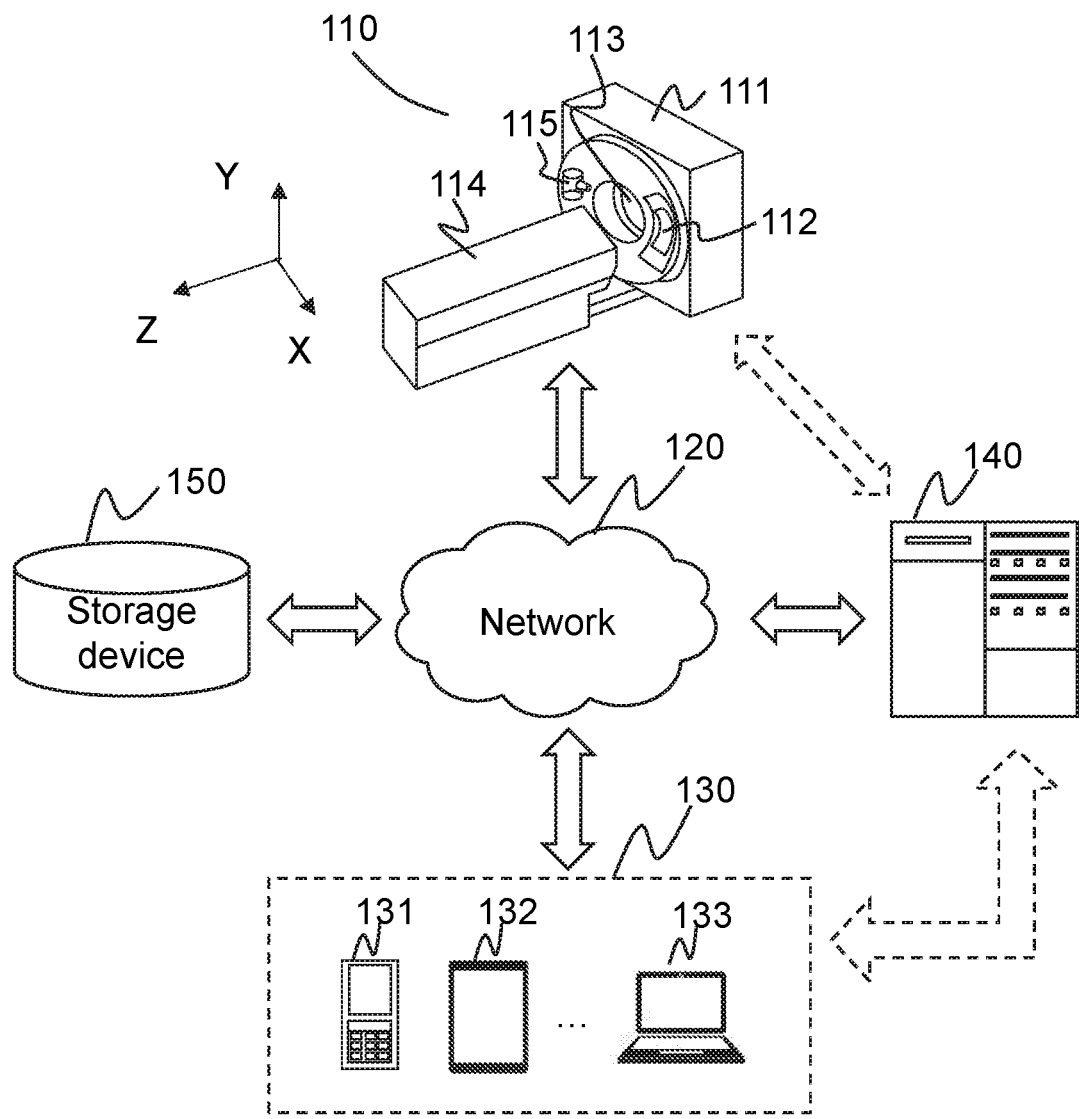
FIG. 1 is a schematic diagram illustrating an exemplary PET system according to some embodiments of the present disclosure.

FIG. 1 is a schematic diagram illustrating an exemplary imaging system 100 according to some embodiments of the present disclosure. In some embodiments, imaging system 100 may be a single modality system. For example, imaging system 100 may be a PET system, a CT system, or an ECT system. In some embodiments, imaging system 100 may be a multi-modality system. For example, imaging system 100 may be a positron emission tomography-computed tomography (PET-CT) system, a magnetic resonance-positron emission tomography (MR-PET) system or the like. In some embodiments, imaging system 100 may be a positron emission tomography-computed tomography (PET-CT) system. In some embodiments, imaging system 100 may include a PET-CT scanner 110, a network 120, one or more terminals 130, a processing engine 140, and a storage device 150.

PET-CT scanner 110 may include a gantry 111, a detector 112, a detecting region 113, and a scanning table 114. Gantry 111 may support detector 112. A subject may be placed on scanning table 114 for CT scan and/or PET scan. In some embodiments, PET-CT scanner 110 may include a CT scanner and a PET scanner. When the CT scanner of PET-CT scanner 110 performs a CT scan, a radiation source 115 may emit radioactive rays to the subject. Detector 112 may detect radiation events emitted from detecting region 113 to generate CT data. Detector 112 used in CT scan may include a scintillation detector (e.g., a cesium iodide detector), a gas detector, etc.

Before a PET scan is started, a radionuclide (also referred to as "PET tracer," or "PET tracer molecules") may be introduced into the subject. The PET tracer may emit positrons in the detecting region 113 when it decays. An annihilation (also referred to as an "annihilation event" or a "coincidence event") may occur when a positron collides with an electron. The annihilation may produce two gamma photons, which may travel in opposite directions. The line connecting the two gamma photons may be referred to as a "line of response (LOR)." Detector 112 may detect the annihilation events (e.g., gamma photons) emitted from the detecting region 113 to generate PET data. In some embodiments, detector 112 used in a PET scan may be different from detector 112 used in a CT scan. In some embodiments, detector 112 used in a PET scan may include one or more crystal elements and/or one or more photomultiplier tubes (PMT) (not shown).

Network 120 may include any suitable network that can facilitate the exchange of information and/or data for imaging system 100. In some embodiments, one or more components of imaging system 100 (e.g., PET-CT scanner 110, terminal 130, processing engine 140, storage device 150, etc.) may communicate information and/or data with one or more other components of imaging system 100 via network 120. For example, processing engine 140 may obtain PET data and/or CT data from the PET-CT scanner 110 via network 120. As another example, processing engine 140 may obtain user instructions from terminal 130 via network 120. Network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, network 120 may include one or more network access points. For example, network 120 may include wired and/or wireless network access points such as base stations and/or Internet exchange points through which one or more components of imaging system 100 may be connected to network 120 to exchange data and/or information.

Terminal(s) 130 may include a mobile device 131, a tablet computer 132, a laptop computer 133, or the like, or any combination thereof. In some embodiments, mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, terminal(s) 130 may be part of processing engine 140.

Processing engine 140 may process data and/or information obtained from PET-CT scanner 110, terminal 130, and/or storage device 150. For example, processing engine 140 may process CT data and/or PET data, and reconstruct an image based on the CT data and/or PET data. In some embodiments, processing engine 140 may be a computer, a user console, a single server or a server group, etc. The server group may be centralized or distributed. In some embodiments, processing engine 140 may be local or remote. For example, processing engine 140 may access information and/or data stored in PET-CT scanner 110, terminal 130, and/or storage device 150 via network 120. As another example, processing engine 140 may be directly connected to PET-CT scanner 110, terminal 130 and/or storage device 150 to access stored information and/or data. In some embodiments, processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, processing engine 140 may be implemented by a computing device 200 having one or more components as illustrated in FIG. 2.

Storage device 150 may store data, instructions, and/or any other information. In some embodiments, storage device 150 may store data obtained from PET-CT scanner 110, terminal 130, and processing engine 140. In some embodiments, storage device 150 may store data and/or instructions that processing engine 140 may execute or use to perform exemplary methods described in the present disclosure. In some embodiments, storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, storage device 150 may be connected to network 120 to communicate with one or more other components in imaging system 100 (e.g., processing engine 140, terminal 130, etc.). One or more components in imaging system 100 may access the data or instructions stored in storage device 150 via network 120. In some embodiments, storage device 150 may be directly connected to or communicate with one or more other components in imaging system 100 (e.g., processing engine 140, terminal 130, etc.). In some embodiments, storage device 150 may be part of processing engine 140.

FIG. 2 is a schematic diagram illustrating hardware and/or software components of an exemplary computing device 200 on which processing engine 140 may be implemented according to some embodiments of the present disclosure. As illustrated in FIG. 2, computing device 200 may include a processor 210, a storage 220, an input/output (I/O) 230, and a communication port 240.

Processor 210 may execute computer instructions (e.g., program code) and perform functions of processing engine 140 in accordance with techniques described herein. The computer instructions may include, for example, routines, programs, objects, components, data structures, procedures, modules, and functions, which perform particular functions described herein. For example, processor 210 may process image data obtained from PET-CT scanner 110, terminal 130, storage device 150, and/or any other component of imaging system 100. In some embodiments, processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in computing device 200. However, it should be noted that computing device 200 in the present disclosure may also include multiple processors. Thus operations and/or method steps that are performed by one processor as described in the present disclosure may also be jointly or separately performed by the multiple processors. For example, if in the present disclosure the processor of computing device 200 executes both step A and step B, it should be understood that step A and step B may also be performed by two or more different processors jointly or separately in computing device 200 (e.g., a first processor executes step A and a second processor executes step B, or the first and second processors jointly execute steps A and B).

Storage 220 may store data/information obtained from PET-CT scanner 110, terminal 130, storage device 150, and/or any other component of imaging system 100. In some embodiments, storage 220 may include a mass storage, removable storage, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random-access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, storage 220 may store one or more programs and/or instructions to perform exemplary methods described in the present disclosure. For example, storage 220 may store a program for processing engine 140 for determining a regularization item.

I/O 230 may input and/or output signals, data, information, etc. In some embodiments, I/O 230 may enable a user interaction with processing engine 140. In some embodiments, I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

Communication port 240 may be connected to a network (e.g., network 120) to facilitate data communications. Communication port 240 may establish connections between processing engine 140 and PET-CT scanner 110, terminal 130, and/or storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, communication port 240 may be and/or include a standardized communication port, such as RS232, RS485, etc. In some embodiments, communication port 240 may be a specially designed communication port. For example, communication port 240 may be designed in accordance with the digital imaging and communications in medicine (DICOM) protocol.

Figure 3:
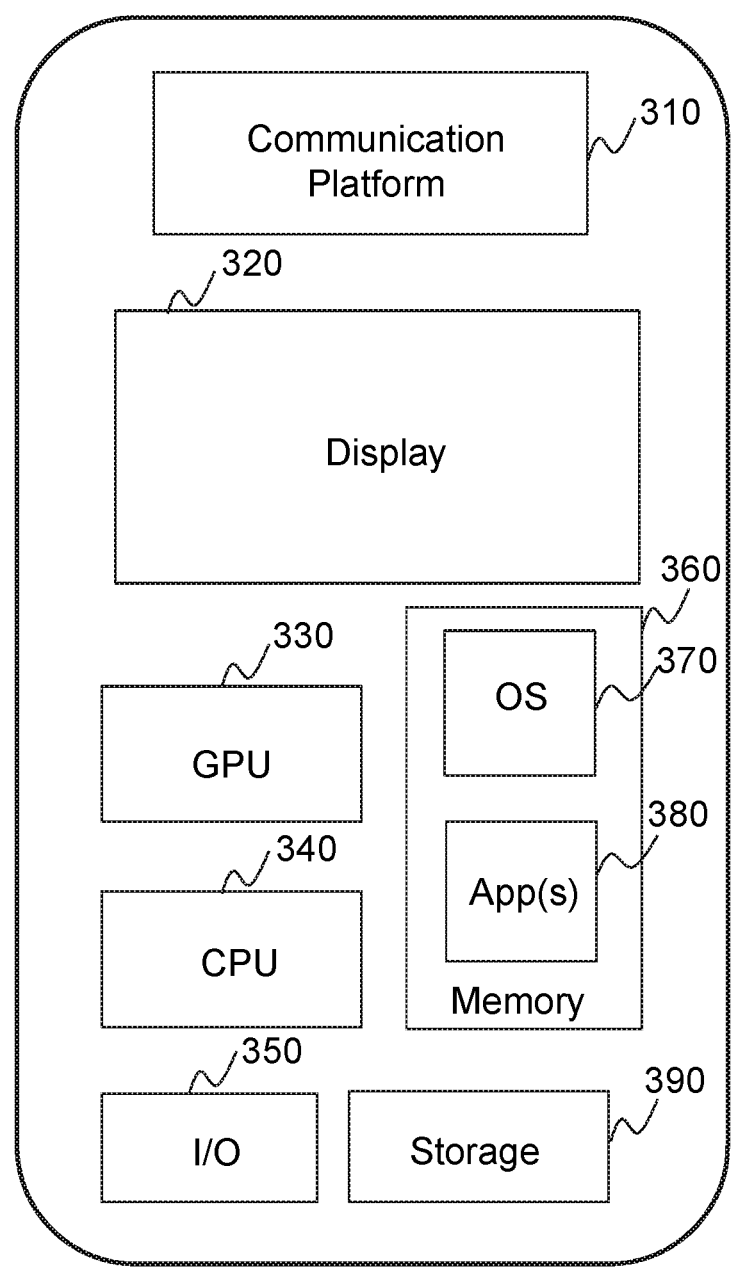
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device 300 on which terminal 130 may be implemented according to some embodiments of the present disclosure. As illustrated in FIG. 3, mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in mobile device 300. In some embodiments, a mobile operating system 370 (e.g., iOS™, Android™, Windows Phone™, etc.) and one or more applications 380 may be loaded into memory 360 from storage 390 in order to be executed by CPU 340. Applications 380 may include a browser or any other suitable mobile apps for receiving and rendering information relating to image processing or other information from processing engine 140. User interactions with the information stream may be achieved via I/O 350 and provided to processing engine 140 and/or other components of imaging system 100 via network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
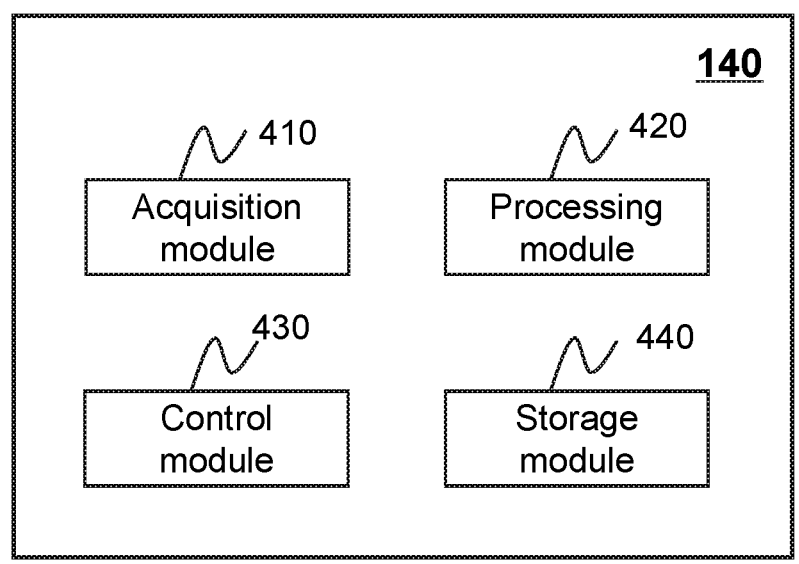
FIG. 4 is a block diagram illustrating an exemplary processing engine according to some embodiments of the present disclosure.

FIG. 4 is a block diagram illustrating an exemplary processing engine 140 according to some embodiments of the present disclosure. Processing engine 140 may include an acquisition module 410, a processing module 420, a control module 430, and a storage module 440.

Acquisition module 410 may acquire data related to PET imaging. Acquisition module 410 may acquire data from PET-CT scanner 110, terminal 130, storage device 150, and/or an external data source (e.g., a cloud data center) via network 120. Data related to PET imaging may include CT data, PET data, CT images, PET images, scout images, reconstruction algorithms, user instructions, programs, scanning parameters, or the like, or a combination thereof. In some embodiments, acquisition module 410 may acquire CT data and/or PET data from detector 112 of PET-CT scanner 110.

More particular, CT data may indicate attenuation information of an imaged subject. In some embodiments, CT data acquired by acquisition module 410 may include sparse projection data, limited-range projection data, low-dose projection data, local projection data, incomplete projection data, or the like. In some embodiments, the CT data may be generated by performing multiple projections at different angles around an imaged subject. For example, the CT data may be generated by performing projections at sparse angles to reduce radiation dose. PET data may associate with concentration and spatial location of radionuclides (also referred to as "positron emitters") within the imaged subject. In some embodiments, acquisition module 410 may transmit acquired data to processing module 420 for imaging and/or further processing, or storage module 440 for storage.

Processing module 420 may process data provided by various components or devices of imaging system 100. Processing module 420 may obtain data acquired by acquisition module 410, data retrieved from storage module 440, etc. In some embodiments, processing module 420 may process acquired CT data and/or PET data. For example, CT data obtained from acquisition module 410 may be filtered according to a Gaussian approach in order to remove or reduce noise in the CT data. In some embodiments, processing module 420 may reconstruct CT images based on CT data, or reconstruct PET images based on CT data and PET data according to one or more reconstruction algorithms. Exemplary reconstruction algorithm may include an ordered subset expectation maximization (OSEM) algorithm, an iterative reconstruction algorithm (e.g., a statistical reconstruction algorithm), a Fourier slice theorem algorithm, a filtered back projection (FBP) algorithm, an analytic reconstruction algorithm, or the like, or any combination thereof.

In some embodiments, processing module 420 may generate reports including one or more Images and/or other related information, and/or perform any other function for image reconstruction in accordance with various embodiments of the present disclosure. For example, processing module 420 may determine a PET imaging area and a CT scan area to obtain PET data and CT data respectively, and reconstruct a PET image based on the PET data and the CT data. As another example, processing module 420 may determine a pre-scan area, and expand the pre-scan area to obtain a PET imaging area and a CT scan area.

Control module 430 may control operations of one or more components or devices of imaging system 100. In some embodiments, control module 430 may control operations of PET-CT scanner 110 during an imaging scan. For example, control module 430 may control PET-CT scanner 110 to acquire CT data and/or PET data from a plurality of predetermined areas. In some embodiments, control module 430 may control operations of acquisition module 410, storage module 440, and/or processing module 420, for example, by generating one or more control parameters. For example, control module 430 may control processing module 420 to process PET/CT data acquired by acquisition module 410.

In some embodiments, control module 430 may include an interface (e.g., an I/O port). Via the interface, control module 430 may receive a real-time command or retrieve a predetermined command (e.g., provided by a user) to control one or more operations of imaging system 100. For example, control module 430 can render acquisition module 410 and/or processing module 420 to generate images of an imaged subject according to the real-time command and/or the predetermined command. In some embodiments, control module 430 may communicate with one or more other modules of processing engine 140 for exchanging information and/or data.

Storage module 440 may facilitate data storage. Data stored in storage module 440 may include PET/CT data, control parameters, processed PET/CT data, PET/CT images, algorithms, programs, instructions, or the like, or a combination thereof. In some embodiments, storage module 440 may store one or more programs and/or instructions to be executed by one or more processors of computing device 200 to perform exemplary methods described in this disclosure. For example, storage module 440 may store program(s) and/or instruction(s) that can be executed by the processor(s) of computing device 200 to acquire PET/CT data, reconstruct a PET image based on the CT data and the PET data, and/or display any intermediate result or a resultant image.

In some embodiments, one or more modules illustrated in FIG. 4 may be implemented in at least part of the exemplary imaging system 100 as illustrated in FIG. 1. For example, acquisition module 410, processing module 420, control module 430, and/or storage module 440 may be integrated into a console (not shown). Via the console, a user may set parameters for scanning an object, controlling an imaging process, controlling parameters for reconstruction of an image, viewing reconstructed images, etc. In some embodiments, the console may be implemented via processing engine 140 and/or terminal 130.

Figure 5:
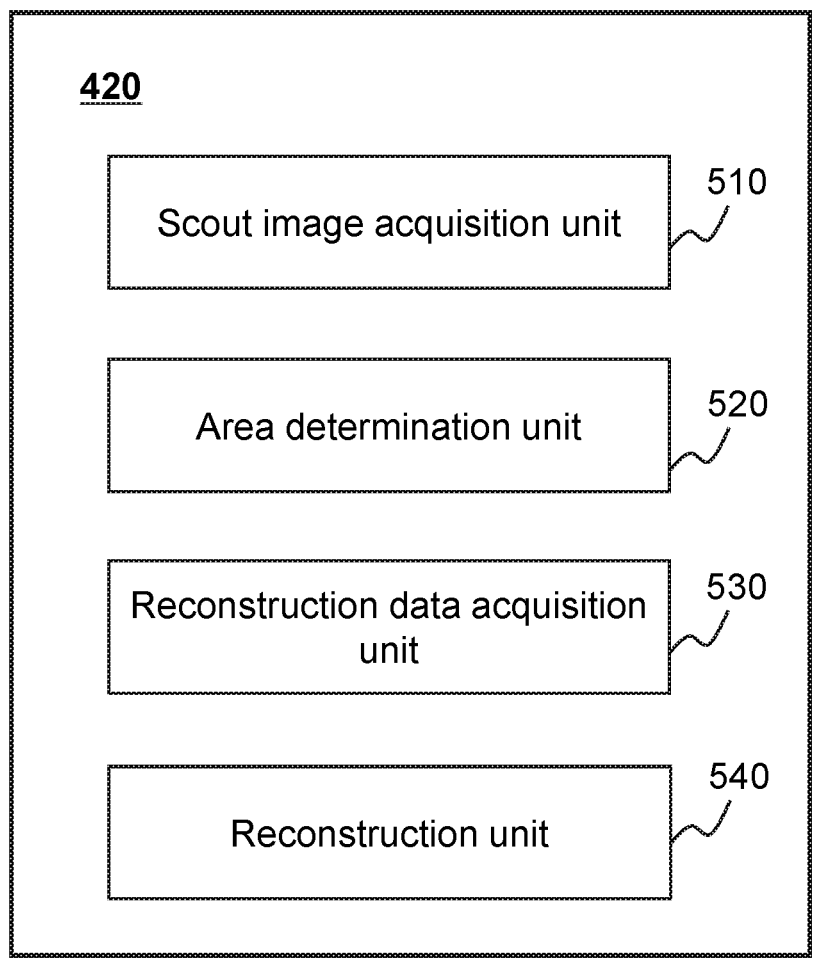
FIG. 5 is a block diagram illustrating an exemplary processing module according to some embodiments of the present disclosure.

FIG. 5 is a block diagram illustrating an exemplary processing module 420 according to some embodiments of the present disclosure. Processing module 420 may include a scout image acquisition unit 510, an area determination unit 520, a reconstruction data acquisition unit 530, and a reconstruction unit 540. One or more components of processing module 420 may be implemented on various devices (e.g., processor 210 of computing device 200 as illustrated in FIG. 2).

Scout image acquisition unit 510 may acquire a scout image. The scout image may be used as an overview of the scanning table 114 or an imaged subject (e.g., a patient, a phantom) In some embodiments, the scout image may include a CT scout image, an optical image, a thermal infrared image, a virtual image, or the like, or a combination thereof. In some embodiments, the scout image may be a CT scout image. The CT scout image may be obtained based on a CT scout scan. During the CT scout scan, PET-CT scanner 110 may scan the target object on scanning table 114 by moving scanning table 114 along a longitudinal direction (i.e., Z-direction illustrated in FIG. 1) with radiation source 115 and detector 112 staying stationary. Alternatively, the scout image may be an image captured by a camera, which may be arranged on PET-CT scanner 110. The camera arranged on PET-CT scanner 110 may generate a scout image by taking a photo of the target object.

In some embodiments, scout image acquisition unit 510 may acquire a scout image from one or more terminals 130, storage device 150 via network 120. The scout image may be a two-dimensional (2D) image or a three-dimensional (3D) image. In some embodiments, the acquired scout image may be transmitted to area determination unit 520 and/or reconstruction unit 540 for further processing, or transmitted to a storage unit (not shown) or any storage device disclosed elsewhere in the present disclosure for storage.

Area determination unit 520 may determine a plurality of areas for imaging. In some embodiments, area determination unit 520 may obtain a pre-scan area. The pre-scan area may refer to a preliminary area from which PET/CT data may be acquired. In some embodiments, the pre-scan area may be selected by a user (e.g., by, for example, an input device), or generated according to default settings of imaging system 100, or a combination of both. In some embodiments, area determination unit 520 may determine the first area and/or the second area by, for example, expanding the pre-scan area in certain directions. Merely for illustration purposes, area determination unit 520 may determine the first area by expanding the pre-scan area in all directions until the pre-scan area has a same size as the scout scan area. Area determination unit 520 may determine the second area by expanding the pre-scan area in certain directions until the pre-scan area accommodates the target object. Details regarding the determination of the first area and the second area may be described elsewhere in the present disclosure (e.g., FIGS. 7-11 and the descriptions thereof).

The areas determined by area determination unit 520 may include two-dimensional areas or three-dimensional areas (also referred to as "volumes") having certain sizes, shapes, and/or locations. In some embodiments, the size, shape, and/or location of a PET imaging area or a CT scan area may relate to an imaged subject (e.g., a patient or a phantom). Merely for illustration purposes, the size of the CT scan area may be suitable for accommodating the imaged subject.

Reconstruction data acquisition unit 530 may obtain PET data and/or CT data from a plurality of areas determined by area determination unit 520. In some embodiments, reconstruction data acquisition unit 530 may obtain the PET data associated with the first area by detecting annihilation events initiated from the first area. In some embodiments, the PET data may include physiological metabolism information of the target object. In some embodiments, reconstruction data acquisition unit 530 may obtain the CT data associated with the second area by performing a CT scan (e.g., a spiral scan) on the second area. The CT data may indicate attenuation information of the second area. In some embodiments, the attenuation information of the second area may include attenuation information of the target object, scanning table 114, and air in the second area.

Reconstruction unit 540 may reconstruct an image. In some embodiments, reconstruction unit 540 may reconstruct a CT image of an imaged subject based on CT data, or reconstruct a PET image of an imaged subject based on PET data and CT data. In some embodiments, the PET data and the CT data may be obtained by reconstruction data acquisition unit 530 or stored in storage module 440.

Reconstruction unit 540 may reconstruct a CT image of an imaged subject according to a CT reconstruction technique. Exemplary CT reconstruction technique may include an iterative reconstruction (e.g., a statistical reconstruction), a Fourier slice theorem, a filtered back projection (FBP), a fan-beam reconstruction, an analytic reconstruction, or the like, or any combination thereof. Reconstruction unit 540 may reconstruct a PET image of an imaged subject according to a PET reconstruction technique. Exemplary PET reconstruction technique may include a p-filtered layer gram, a Maximum Likelihood Expectation Maximization (ML-EM), an Ordered Subset Expectation Maximization (OSEM), a Row-Action Maximum Likelihood Algorithm (RAMLA), or the like, or any combination thereof.

It should be noted that the above description of the processing module is merely provided for the purposes of illustration, and not intended to limit the scope of the present disclosure. For persons having ordinary skills in the art, multiple variations or modifications may be made under the teachings of the present disclosure. For example, one or more units in processing module 420 may include an independent storage block (not shown) respectively. As another example, any two or more units may be combined as an independent unit used to implement more than one functions. As still another example, any one of the units may be divided into two or more sub-units. However, those variations and modifications do not depart from the scope of the present disclosure.

Figure 6:
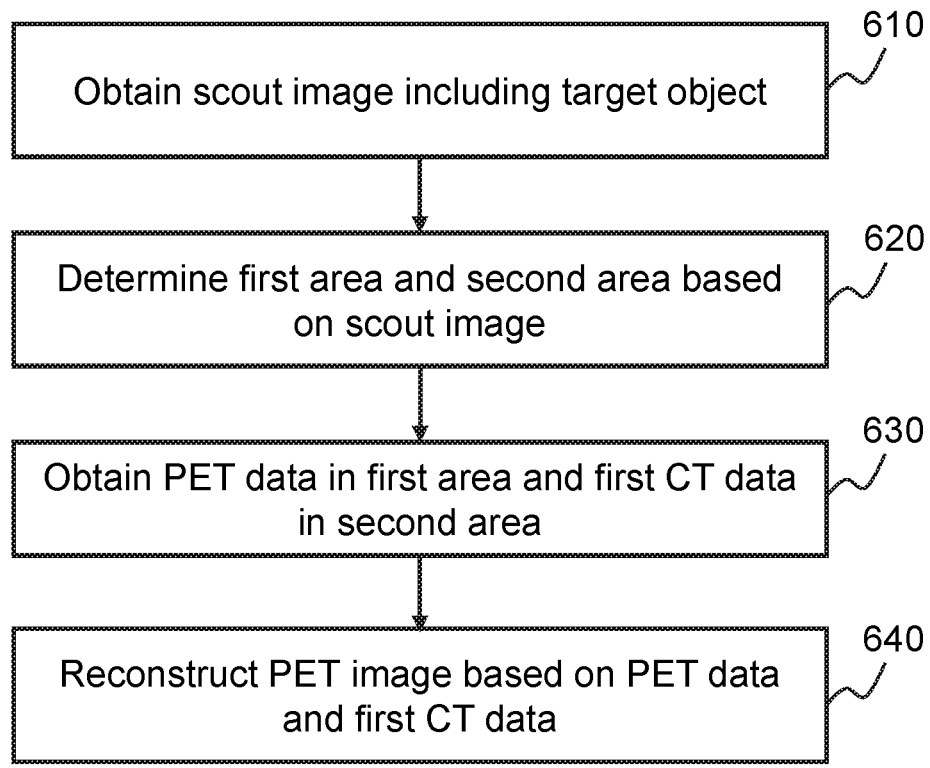
FIG. 6 is a flowchart illustrating an exemplary process for reconstructing a PET image according to some embodiments of the present disclosure.

FIG. 6 is a flowchart illustrating an exemplary process for reconstructing a PET image according to some embodiments of the present disclosure. In some embodiments, at least part of process 600 may be performed by one or more components in processing engine 140.

In 610, a scout image including a target object may be obtained. The scout image may be obtained by, for example, scout image acquisition unit 510. The scout image may include a CT scout image, an optical image, a thermal infrared image, a virtual image, or the like, or a combination thereof. In some embodiments, the scout image may be a CT scout image. The CT scout image may be obtained based on a CT scout scan. During the CT scout scan, PET-CT scanner 110 may scan the target object on scanning table 114 by moving scanning table 114 along a longitudinal direction (i.e., the Z-direction illustrated in FIG. 1) with radiation source 115 and detector 112 staying stationary. Alternatively, the scout image may be an image captured by a camera, which may be arranged on PET-CT scanner 110. The camera arranged on PET-CT scanner 110 may generate a scout image by taking a photo of the target object. The target object may be a patient, a part of a patient, a phantom, a part of a phantom, or the like, or a combination thereof.

The scout image may correspond to a scout scan area. In some embodiments, the scout scan area may encompass scanning table 114 as well as the target object on scanning table 114. The size of the target object and/or position of the target object relative to scanning table 114 may be determined based on the scout image.

In 620, a first area and a second area may be determined based on the scout image. The first area and the second area may be determined by, for example, area determination unit 520. In some embodiments, the first area may be a PET imaging area. Imaging system 100 may obtain PET data in the first area and reconstruct a PET image of the first area. In some embodiments, the second area may be a CT scan area. Imaging system 100 may obtain CT data associated with the second area. In some embodiments, the first area and/or the second area may be the same as or smaller than the scout scan area. In some embodiments, the second area may be located in the first area. An area being located in the first area and differing from the second area may be defined as a third area (i.e., the first area may be composed of the second area and the third area).

In some embodiments, area determination unit 520 may obtain a pre-scan area before the first area and the second area are determined. The pre-scan area may be selected by a user (e.g., by, for example, an input device) or generated according to default settings of imaging system 100, or a combination of both. For example, when a scout image is displayed on a screen of terminal 130 or a console, a user may input a pre-scan window (e.g., a rectangle box) on the scout image, and adjust a location and a size of the pre-scan window by, for example, touching the screen. The pre-scan window may correspond to a pre-scan area. The first area and/or the second area may be determined by, for example, expanding the pre-scan area in certain directions. Merely for illustration purposes, imaging system 100 may determine the first area by expanding the pre-scan area in all directions until the pre-scan area has the same size as the scout scan area. Imaging system 100 may determine the second area by expanding the pre-scan area in certain directions until the pre-scan area accommodates the target object. Details regarding the determination of the first area and the second area may be described elsewhere in the present disclosure (e.g., FIGS. 7-11 and the descriptions thereof).

In 630, PET data in the first area may be obtained, and first CT data in the second area may be obtained. The PET data and the CT data may be obtained by, for example, the reconstruction data acquisition unit 530. In some embodiments, imaging system 100 may obtain the PET data in the first area by detecting annihilation events initiated from the first area. In some embodiments, the PET data may include physiological metabolism information of the target object. In some embodiments, imaging system 100 may obtain the CT data in the second area by performing a CT scan (e.g., a spiral scan) on the second area. The CT data may indicate attenuation information of the second area. In some embodiments, the attenuation information of the second area may include attenuation information of the target object, scanning table 114, and air in the second area.

In 640, a PET image may be reconstructed based the first CT data and the PET data. The PET image may be reconstructed by, for example, reconstruction unit 540. In some embodiments, imaging system 100 may obtain second CT data. The second CT data may include attenuation information of the third area. In some embodiments, an attenuation image of first scan area may be generated based on the first CT data and the second CT data, which include attenuation information of the second area and the third area, respectively. The PET image with respect to the first area may be reconstructed based on the attenuation image and the PET data associated with the first area.

In some embodiments, imaging system 100 may obtain the second CT data by performing a CT scan (e.g., a spiral scan) on an area including the third area, such as the first area, the scout scan area, etc. The second CT data may be obtained before the target object (e.g., a patient) is scanned. For example, the second CT data may include attenuation information relating to air and the scan bed, and may include certain preset data. As another example, the second CT data may be obtained at a regular interval (e.g., a day, a week, a month, or a year). The second CT data may not include attenuation information of the target object. In some embodiments, the second CT data may include attenuation information of scanning table 114 and air in the third area. In some embodiments, the second CT data may be stored in storage device 150, storage 220, or any other devices, modules or units capable of storing data. For example, the second CT data may be stored in cloud storage communicating with imaging system 100 via network 120.

The PET image may be reconstructed according to one or more reconstruction techniques. Exemplary PET reconstruction technique may include a p-filtered layer gram, a Maximum Likelihood Expectation Maximization (ML-EM), an Ordered Subset Expectation Maximization (OSEM), a Row-Action Maximum Likelihood Algorithm (RAMLA), or the like, or any combination thereof.

Figure 7:
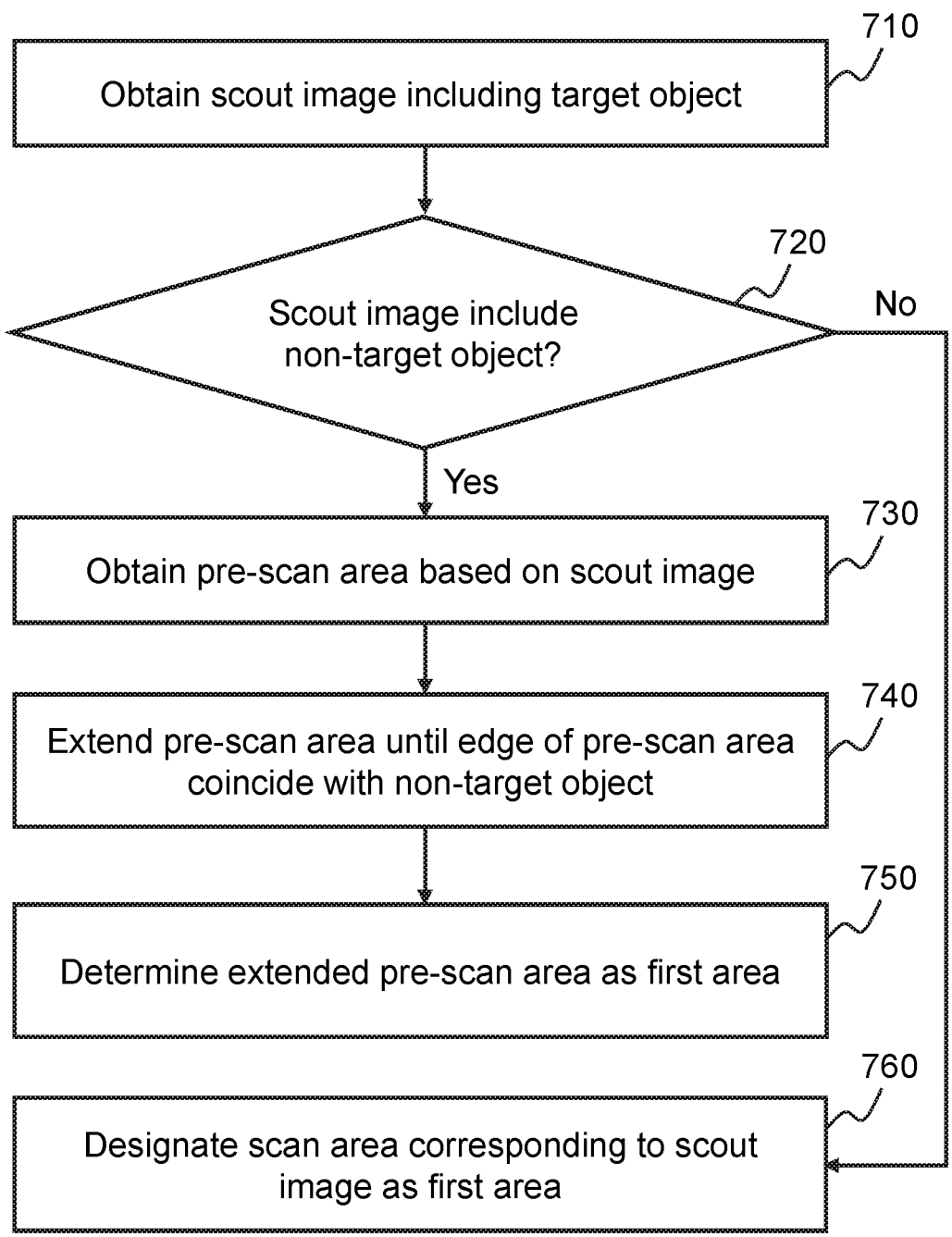
FIG. 7 is a flowchart illustrating an exemplary process for determining a first scan area according to some embodiments of the present disclosure.

FIG. 7 is a flowchart illustrating an exemplary process for determining a first area according to some embodiments of the present disclosure. In some embodiments, the determination of the first area in 620 of process 600 as illustrated in FIG. 6 may be performed based on process 700 illustrated in FIG. 7. In some embodiments, process 700 may be executed by imaging system 100. For example, process 700 may be implemented as a set of instructions stored in a non-transitory storage medium of processing engine 140. Processor 210 may execute the set of instructions and perform the operations of process 700 accordingly.

In 710, a scout image including a target object may be obtained. The scout image may be obtained by, for example, scout image acquisition unit 510. The scout image may include a CT image, an image captured by a camera, etc. The scout image may be a scout view of a scout scan area. In some embodiments, the scout scan area may encompass scanning table 114 as well as the target object on scanning table 114. The size of the target object and/or the position of the target object relative to scanning table 114 may be determined based on the scout image. The target object may be a patient, a part of a patient, a phantom, a part of a phantom, or the like, or a combination thereof. For example, as shown is FIG. 10A, a patient 1010 may be placed on a scanning table 1020. Patient 1010 may be determined as the target object. When an imaging scan is performed, scanning table 1020 together with patient 1010 may be moved into a PET scanning FOV P1. The PET scanning FOV refers to an observable area of the PET scanner of PET-CT scanner 110. Scout image acquisition unit 510 may obtain a scout image including the target object (i.e., patient 1010). The scout image may correspond to a scout scan area D1. Area determination unit 520 may obtain a pre-scan area D2 based on the scout image. As another example, as shown is FIG. 11A, a target object 1110 and a non-target object 1130 may be placed on a scanning table 1120. Target object 1110 may be, for example, a patient. Non-target object 1130 may be, for example, a phantom. When an imaging scan is performed, scanning table 1120 together with target object 1110 may be moved into a PET scanning FOV P1.

In 720, a determination as to whether the scout image also includes a non-target object. If area determination unit 520 determines that the scout image does not include a non-target object, process 700 may proceed to 760 to determine (or designate) the scout scan area corresponding to the scout image as the first area. If area determination unit 520 determines that the scout image includes a non-target object, process 700 may proceed to 730 to obtain a pre-scan area based on the scout image. A non-target object refers to an object that is not the target object in the operations. For example, if a patient is determined as a target object, another object (e.g., a phantom) in the scout image except scanning table 114 may be defined as a non-target object in this operation. As another example, for a patient with liver cancer, the chest of the patient may be determined as a target object, and the abdomen and the neck of the patient may be determined as non-target objects.

Figure 11A:
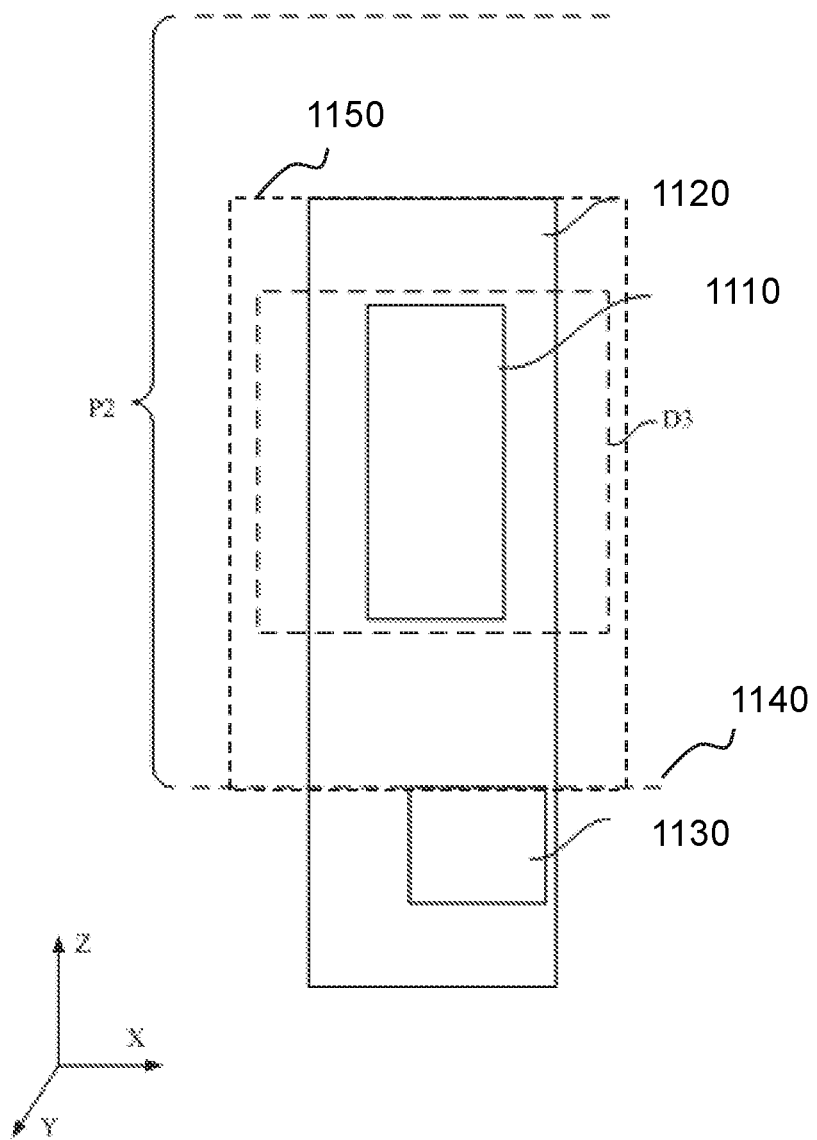
FIG. 11A is a schematic diagram illustrating a determination of a first scan area and a second scan area according to some embodiments of the present disclosure.
Figure 11B:
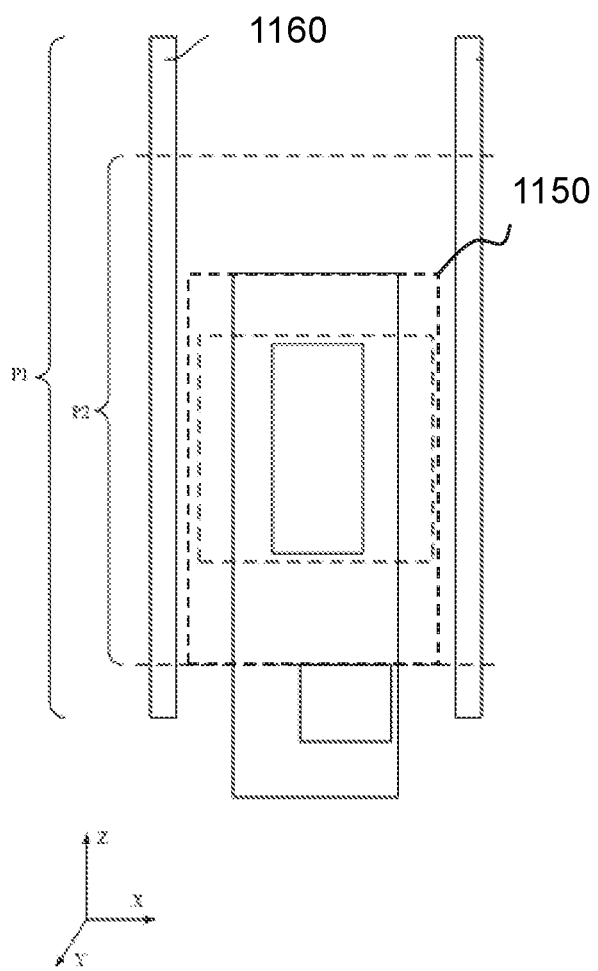
FIG. 11B is a schematic diagram illustrating a determination of a location for a first scan area according to some embodiments of the present disclosure.

In 730, a pre-scan area may be obtained based on the scout image. The pre-scan area may be obtained by, for example, area determination unit 520. The pre-scan area may have a certain shape. For example, the pre-scan area may have a shape of a square, a rectangle, a circle, an oval, or the like. In some embodiments, the pre-scan area may have a shape of a rectangle. For example, as illustrated in FIGS. 11A and 11B, area determination unit 520 may obtain a scout image including target object 1110 and non-target object 1130. Area determination unit 520 may obtain a pre-scan area (not shown) based on the scout image.

In some embodiments, the pre-scan area may be determined by a user (e.g., a radiologist). For example, when a scout image is displayed on a screen of terminal 130 or a console, a user may input a pre-scan window (e.g., a rectangle box) on the scout image and adjust the location and/or size of the pre-scan window by, for example, touching the screen. The pre-scan window may correspond to the pre-scan area. In some embodiments, the pre-scan area may encompass the target object or at least a portion of the target object. In some embodiments, the pre-scan area may be determined by imaging system 100. For example, imaging system 100 may use a machine learning technology to train a pre-scan area determination model. When a user inputs a word representing a body part (e.g., "chest") via an interface (e.g., display 320 of mobile device 300), imaging system 100 may automatically determine the pre-scan area corresponding to the chest of the patient based on the trained area determination model.

In 740, the pre-scan area may be expanded until an edge of the pre-scan area coincides with (or cross) a boundary of the non-target object. The pre-scan area may be expanded by, for example, area determination unit 520. The pre-scan area may be expanded in various directions. In some embodiments, the pre-scan area may include a two-dimensional area. Alternatively or additionally, the pre-scan area may refer to a three-dimensional volume. Merely for illustration purposes, a two-dimensional pre-scan area may be represented by a rectangular area. The rectangular area may be expanded in four directions. The four directions may be perpendicular to four sides of the rectangular area, respectively. In some embodiments, the pre-scan area may be expanded in different directions over different distances. For example, the pre-scan area may be expanded in a first direction over a first distance and may be expanded in a second direction over a second distance. The distance over which the pre-scan area is expanded may associate with the non-target object. More particularly, if area determination unit 520 determines that a non-target object is located on a direction in which the pre-scan area is expanded, area determination unit 520 may terminate the expansion of the pre-scan area in that direction when an edge of the pre-scan area coincides with (or cross) a boundary of the non-target object. If area determination unit 520 determines that a non-target object is not located on a direction in which the pre-scan area is expanded, area determination unit 520 may terminate the expansion of the pre-scan area in that direction when an edge of the pre-scan area coincides with (or cross) an edge of the scout scan area. For example, as illustrated in FIG. 11A, non-target object 1130 may be positioned in a negative direction along the Z-axis. The pre-scan area may be expanded in the negative direction along the Z-axis until an edge of the pre-scan area coincides with (or cross) a boundary of non-target object 1130. Area determination unit 520 may terminate the expansion of the pre-scan area at location 1140.

In some embodiments, the pre-scan area may be expanded in a direction (e.g., negative direction along Z-axis as shown in FIGS. 11A and 11B) in stepwise. Each step may have a certain length, for example, 5 millimeters, 2 centimeters, 10 centimeters, or the like. Area determination unit 520 may determine whether an edge of the pre-scan area coincides with (or cross) an edge of the non-target object or an edge of the scout scan area after each step. If area determination unit 520 determines that an edge of the pre-scan area coincides with (or cross) an edge of the non-target object or an edge of the scout scan area, area determination unit 520 may terminate the expansion of the pre-scan area.

In 750, the expanded pre-scan area may be determined (or designated) as the first area. After area determination unit 520 terminates the expansion of the pre-scan area, area determination unit 520 may determine (or designate) the expanded pre-scan area as the first area (i.e., the PET imaging area). Imaging system 100 may obtain PET data associated with the first area and reconstruct a PET image of the first area based on obtained PET data. For example, as illustrated in FIG. 11A, the expanded scan area may be determined or designated as a first area 1150 (i.e., a PET imaging area) to obtain PET data and reconstruct a PET image.

Figure 10A:
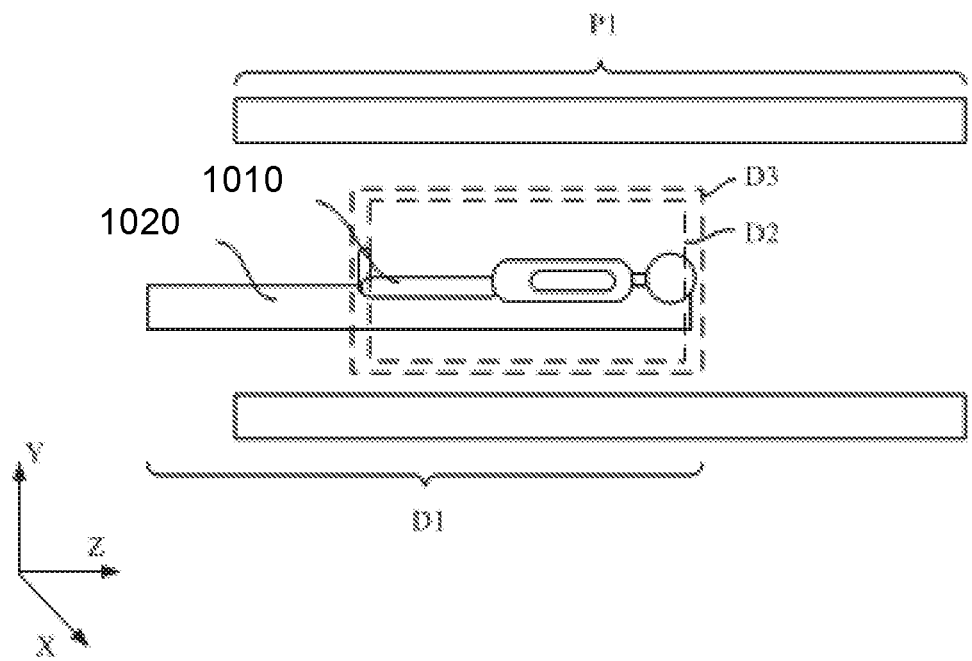
FIG. 10A is a schematic diagram illustrating a determination of a first scan area and a second scan area according to some embodiments of the present disclosure.
Figure 10B:
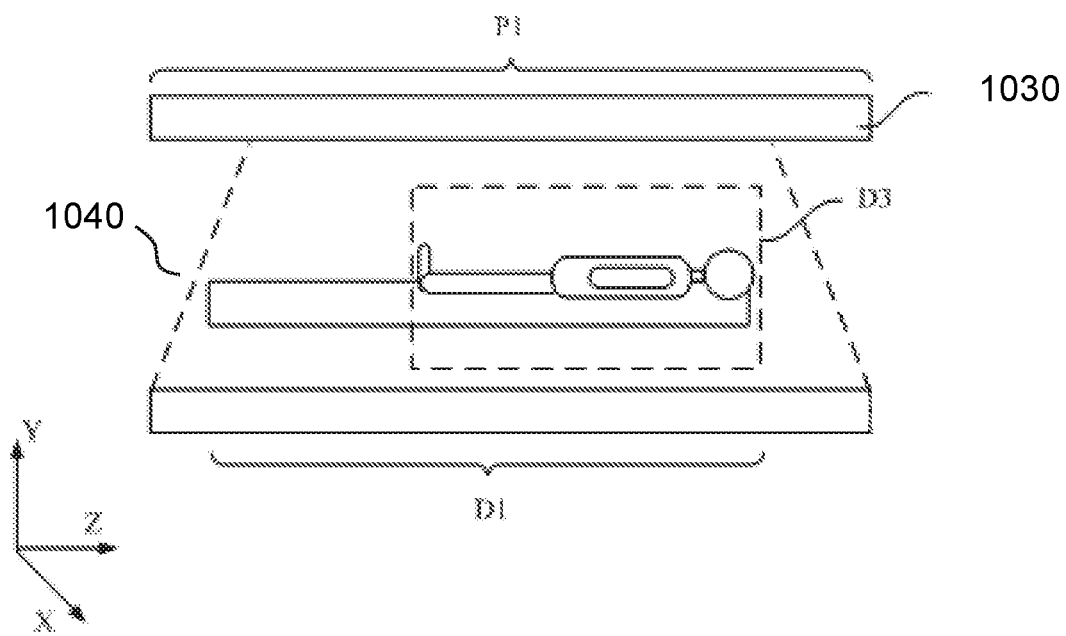
FIG. 10B is a schematic diagram illustrating a determination of a location for a first scan area according to some embodiments of the present disclosure.

In 760, a scan area corresponding to the scout image may be designated as the first area. The scan area corresponding to the scout image may refer to the scout scan area. If area determination unit 520 determines that the scout image does not include the non-target object, area determination unit 520 may determine the scout scan area as the first area. For example, as illustrated in FIGS. 10A and 10B, the scout scan area D1 may not include a non-target object. The scout scan area D1 may be designated as the first area (i.e., the PET imaging area) to obtain PET data and reconstruct a PET image.

Figure 8:
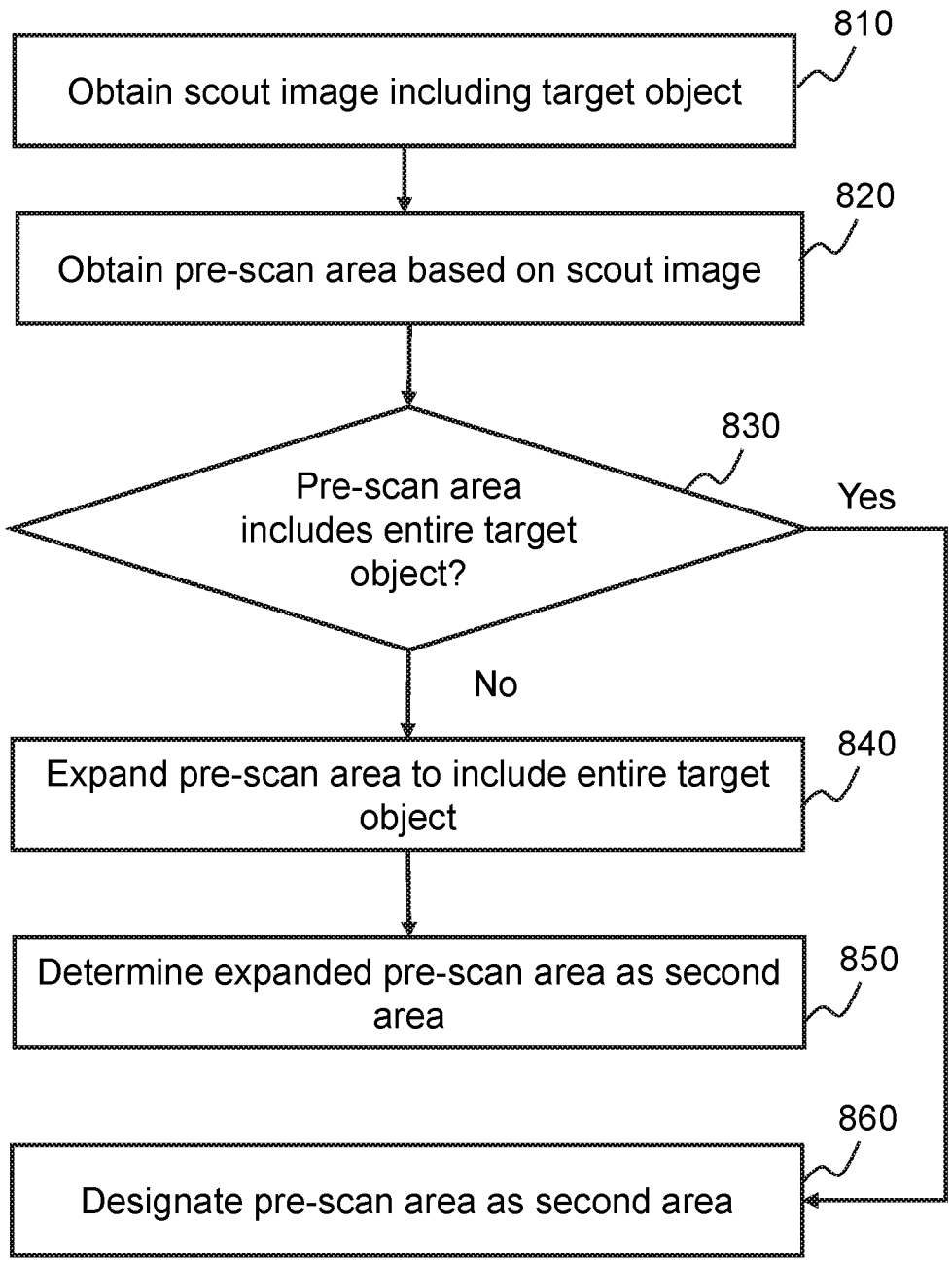
FIG. 8 is a flowchart illustrating an exemplary process for determining a second scan area according to some embodiments of the present disclosure.

FIG. 8 is a flowchart illustrating an exemplary process for determining a second area according to some embodiments of the present disclosure. In some embodiments, the determination of the second area in 620 of process 600 illustrated in FIG. 6 may be performed based on process 800 illustrated in FIG. 8. In some embodiments, process 800 may be implemented as a set of instructions stored in a non-transitory storage medium of processing engine 140. Processor 210 may execute the set of instructions and may perform the operations in process 800 accordingly.

In 810, a scout image including a target object may be obtained. The scout image may be obtained by, for example, scout image acquisition unit 510. In some embodiments, the scout image may be a CT image including the target object. In some embodiments, the scout image may be an image captured by a camera including the target object. The target object may be a patient, a part of a patient, a phantom, a part of a phantom, or the like, or a combination thereof. The scout image may be a scout view of a scout scan area. In some embodiments, the scout scan area may encompass scanning table 114 as well as the target object on scanning table 114. The size of the target object and/or the position of the target object relative to scanning table 114 may be determined based on the scout image. The target object may be a patient, a part of a patient, a phantom, a part of a phantom, or the like, or a combination thereof. For example, as shown is FIG. 10A, patient 1010 may be placed on scanning table 1020. Patient 1010 may be determined as the target object. When an imaging scan is performed, scanning table 1020 together with patient 1010 may be moved into PET scanning FOV P1. Scout image acquisition unit 510 may obtain the scout image including the target object (i.e., patient 1010). The scout image may correspond to the scout scan area D1. Area determination unit 520 may obtain pre-scan area D2 based on the scout image. As another example, as shown is FIG. 11A, target object 1110 and non-target object 1130 may be placed on scanning table 1120. Target object 1110 may be, for example, a patient. Non-target object 1130 may be, for example, a phantom. When an imaging scan is performed, scanning table 1120 together with target object 1110 may be moved into PET scanning FOV P1.

In 820, a pre-scan area may be obtained based on the scout image. The pre-scan area may be obtained by, for example, area determination unit 520. In some embodiments, the pre-scan area may be determined by a user (e.g., a radiologist). For example, when a scout image is displayed on a screen of terminal 130 or a console, a user may input a pre-scan window (e.g., a rectangle box) on the scout image and adjust the location and/or size of the pre-scan window by, for example, touching the screen. The pre-scan window may correspond to the pre-scan area. In some embodiments, the pre-scan area may encompass the target object or at least a portion of the target object. In some embodiments, the pre-scan area may be determined by imaging system 100. For example, imaging system 100 may use a machine learning technology to train a pre-scan area determination model. When a user inputs a word representing a body part (e.g., "chest") via an interface (e.g., display 320 of mobile device 300), imaging system 100 may automatically determine the pre-scan area corresponding to the chest of the patient based on the trained area determination model.

In some embodiments, the pre-scan area may accommodate the entire target object or part of the target object. For example, the entire target object (e.g., the whole body of a patient) may be positioned in the pre-scan area. As another example, the pre-scan area may accommodate part of the target object (e.g., certain body parts of a patient, such as a truncus).

In 830, a determination as to whether the pre-scan area includes the entire target object may be determined. The determination may be determined by, for example, area determination unit 520. If area determination unit 520 determines that the pre-scan area does not include the entire target object, process 800 may proceed to 840 to expand the pre-scan area to accommodate the entire target object. If area determination unit 520 determines that the pre-scan area includes the entire target object, process 800 may proceed to 860 to determine the pre-scan area as a CT scan area. In some embodiments, area determination unit 520 may determine whether the pre-scan area includes the entire target object by detecting edges of the target object using, for example, an infrared camera, an optical camera, etc.

In 840, the pre-scan area may be expanded to include the entire target object. The pre-scan area may be expanded by, for example, area determination unit 520. The pre-scan area may be expanded in various directions. In some embodiments, the pre-scan area may include a two-dimensional area. Alternatively or additionally, the pre-scan area may include a three-dimensional volume. Merely for illustration purposes, a two-dimensional pre-scan area may be represented by a rectangular area. The rectangular area may be expanded in four directions. The four directions may be perpendicular to four sides of the rectangular area, respectively. As illustrated in FIG. 11A, area determination unit 520 may expand the pre-scan area along the X-direction, the Y-direction, and/or the Z-direction. In some embodiments, the pre-scan area may be expanded in in different directions over different distances. For example, the pre-scan area may be expanded in a first direction over a first distance and may be expanded in a second direction over a second distance. The distance over which the pre-scan area is expanded may associate with the target object. If area determination unit 520 determines that a certain part of the target object is outside of the pre-scan area and located on a direction in which the pre-scan area is expanded, area determination unit 520 determines may terminate the expansion of the pre-scan area in that direction when the pre-scan area accommodates the certain part of the target object. If area determination unit 520 determines that none parts of the target object are located in a direction in which the pre-scan area is expanded, the pre-scan area may not be expanded by area determination unit 520 in that direction.

Merely for illustration purposes, as illustrated in FIG. 10A, the pre-scan area D2 may not accommodate the entire target. Area determination unit 520 may expand the pre-scan area from the area D2 to an area D3 to accommodate the target object. The area D3 may be determined and/or designated as a CT scan area to obtain CT data of the target object. Area determination unit 520 may expand the pre-scan area in any directions to accommodate the target object. For example, area determination unit 520 may expand the pre-scan area along the X-direction, the Y-direction, and/or the Z-direction in FIG. 10A to accommodate the target object.

In some embodiments, the pre-scan area may be expanded in a direction in stepwise. Each step may have a certain length, for example, 5 millimeters, 2 centimeters, 10 centimeters, or the like. Area determination unit 520 may determine whether the pre-scan area includes the entire target object after each step. If area determination unit 520 determines that the pre-scan area includes the entire target object, area determination unit 520 may terminate the expansion of the pre-scan area.

In 850, the expanded pre-scan area may be determined (or designated) as the second area. After the pre-scan area is expanded to accommodate the entire target object, area determination unit 520 may determine the expanded pre-scan area as the second area for CT scanning to obtain CT data of the target object (i.e., the CT scan area). For example, as illustrated in FIG. 10A, area determination unit 520 may determine or designate area D3 as the second area obtain CT data of target object 1010.

In 860, the pre-scan area may be designated as the second area. The pre-scan area may be designated as the second area by, for example, area determination unit 520. If area determination unit 520 determines that the pre-scan area includes the entire target object, area determination unit 520 may designate the pre-scan area as the second area (i.e., the CT scan area).

Figure 9:
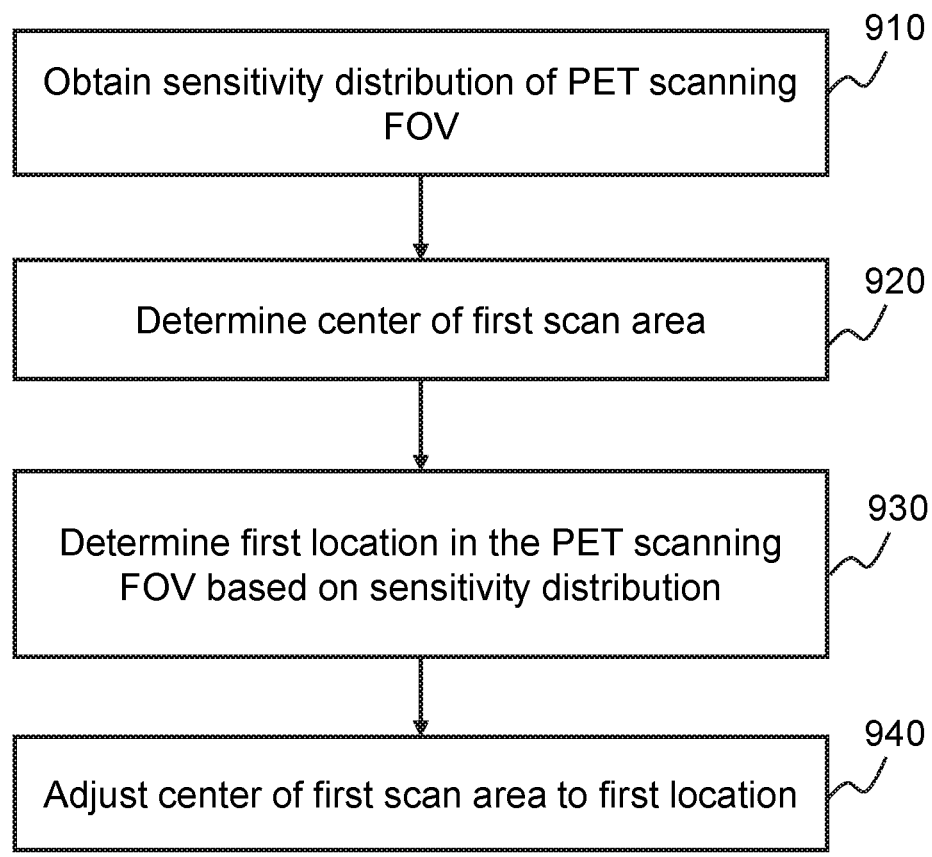
FIG. 9 is a flowchart illustrating an exemplary process for determining a location of the first scan area according to some embodiments of the present disclosure.

FIG. 9 is a flowchart illustrating an exemplary process 900 for determining a location of the first area according to some embodiments of the present disclosure. In some embodiments, process 900 may be executed by imaging system 100. For example, process 900 may be implemented as a set of instructions stored in a non-transitory storage medium of processing engine 140. Processor 210 may execute the set of instructions and may perform the steps in process 900 accordingly.

In 910, a sensitivity distribution of the PET scanning FOV may be obtained. The sensitivity distribution of the PET scanning FOV may be obtained by, for example, acquisition module 410. The PET scanning FOV refers to an observable area of the PET scanner of PET-CT scanner 110. In some embodiments, the sensitivity distribution of the PET scanning FOV may relate to one or more parameters of PET-CT scanner 110. The one or more parameters may include PET scanner length, detector sensitivity, resolution, time window size, or the like. The sensitivity distribution of the PET scanning FOV may correspond to a shape, such as a parabola, a Gaussian curve, a trapezoid, etc. In some embodiments, the sensitivity distribution of the PET scanning FOV may correspond to a shape of a trapezoid in the Y-Z plane as illustrated in FIG. 1.

In 920, the center of the first area may be determined. The center of the first area may be determined by, for example, processing module 420. In some embodiments, the first area may be a PET imaging area. A geometrical center of the PET imaging area may be determined as the center of the first area. For example, the PET imaging area may have a shape of a rectangle, and a geometrical center of the rectangle may be determined as the center of the first area.

In 930, a first location in the PET scanning FOV may be determined based on the sensitivity distribution. The first location in the PET scanning FOV may be determined by, for example, processing module 420. In some embodiments, a location that corresponds to higher sensitivity than other locations in the PET scanning FOV may be determined based on the sensitivity distribution of the PET scanning FOV. In some embodiments, the location that corresponds to a higher sensitivity may be designated as the first location. Merely for illustration purposes, the center of a PET scanning FOV in an axial direction of the PET scanner (e.g., the Z-direction as illustrated in FIG. 1) may correspond to a higher sensitivity with respect to a Gaussian sensitivity distribution. The center of the PET scanning FOV in the axial direction may be determined as the first location.

In some embodiments, a set of first locations corresponding to the same sensitivity may be determined. In some embodiments, the set of first locations may constitute an area. For example, an area surrounding the center of the PET scanning FOV in the axial direction (e.g., the Z-direction as illustrated in FIG. 1) may correspond to a higher sensitivity in a trapezoidal sensitivity distribution. Any locations in the area corresponding to the higher sensitivity in the trapezoidal sensitivity distribution may be designated as the first location.

In 940, the center of the first area may be adjusted to the first location. The center of the first area may be adjusted by, for example, control module 430. The adjustment of the first area may need to make sure that the PET imaging area is located in an area with high sensitivity in the axial direction of the PET scanning FOV. The center of the PET imaging area may be adjusted to the first location for providing higher sensitivity, thereby facilitating PET data acquisition.

In some embodiments, if an area constituted by a plurality of first locations is larger than the first area, the entire first area may be moved into the area when the first area is adjusted to a first location. For example, as illustrated in FIG. 10B, a PET scanner 1030 may have a PET scanning FOV P1. The sensitivity distribution of PET scanning FOV P1 may have a shape of a trapezoid in the Y-Z plane. An area 1040 corresponding to higher sensitivity in the trapezoidal distribution may be determined. As shown in FIG. 10B, area 1040 may be larger than the first scan area. The first area may be adjusted into area 1040 to acquire PET data with higher sensitivity. As another example, as illustrated in FIG. 11B, a PET scanner 1160 may have a PET scanning FOV P1. The sensitivity distribution of PET scanning FOV P1 may have a shape of a trapezoid in Y-Z plane. An area P2 corresponding to higher sensitivity in the trapezoidal distribution may be determined. As illustrated in FIG. 11B, area P2 may be larger than first area 1150. First area 1150 may be adjusted into the trapezoidal distribution to acquire PET data with higher sensitivity.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method implemented on a computing device having at least one processor, the method comprising:
   obtaining, by the at least one processor, a scout image including a target object;
   determining, by the at least one processor, a first area and a second area based on the scout image, wherein the second area is located in the first area;
   obtaining, by the at least one processor, Positron Emission Tomography (PET) data of the first area and first Computed Tomography (CT) data of the second area; and
   reconstructing, by the at least one processor, a PET image with respect to the first area based on the PET data and the first CT data.

2. The method of claim 1, further comprising:
   determining, by the at least one processor, whether the scout image includes a non-target object; and
   determining, by the at least one processor, the first area based on a result of the determination as to whether the scout image includes a non-target object.

3. The method of claim 2, wherein determining the first area based on the result of the determination as to whether the scout image includes a non-target object includes:
   according to a result of the determination that the scout image does not include a non-target object, designating a scan area corresponding to the scout image as the first area.

4. The method of claim 2, wherein determining the first area based on the result of the determination as to whether the scout image includes a non-target object includes:
   according to a result of the determination that the scout image includes a non-target object,
   obtaining a pre-scan area based on the scout image, and
   determining the first area by extending the pre-scan area to a first boundary.

5. The method of claim 4, wherein determining the first area by extending the pre-scan area to the first boundary includes:

determining an edge of the non-target object; and
determining the first boundary according to the edge of the non-target object.

6. The method of claim 1, wherein determining the second area based on the scout image includes:
obtaining a pre-scan area based on the scout image;
determining whether the target object is included in the pre-scan area; and
determining the second area based on a result of the determination as to whether the target object is included in the pre-scan area.

7. The method of claim 6, wherein determining the second area based on a result of the determination as to whether the target object is included in the pre-scan area includes:
according to a result of the determination that the target object is included in the pre-scan area, designating the pre-scan area as the second area.

8. The method of claim 6, wherein determining the second area based on a result of the determination as to whether the target object is included in the pre-scan area includes:
according to a result of the determination that the target object is not included in the pre-scan area, determining the second area by extending the pre-scan area to a second boundary.

9. The method of claim 8, wherein determining the second area by extending the pre-scan area to the second boundary includes:
determining an edge of the target object; and
determining the second boundary according to the edge of the target object.

10. The method of claim 1, further comprising:
determining a third area based on the scout image, the third area being located in the first area and differing from the second area;
obtaining attenuation information of the third area; and
reconstructing, by the at least one processor, the PET image with respect to the first area based on the PET data, the first CT data, and the attenuation information of the third area.

11. The method of claim 10, wherein obtaining the attenuation information of the third area includes:
obtaining attenuation information of a scanning table and air in the third area.

12. The method of claim 1, wherein the scout image is a CT image or an optical image.

13. The method of claim 1, wherein determining the first area based on the scout image includes:
obtaining a sensitivity distribution of a PET scanning field-of-view (FOV); and
determining the first area based on the scout image and the sensitivity distribution.

14. The method of claim 13, wherein determining the first area based on the scout image and the sensitivity distribution includes:
determining a center of the first area;
determining a first location in the PET scanning FOV based on the sensitivity distribution; and
adjusting the center of the first area to the first location.

15. The method of claim 1, wherein determining the first area based on the scout image includes:
determining a center of a PET scanning field-of-view (FOV); and
adjusting the first area to the center of the PET scanning FOV.

16. A system, comprising:
a storage device including a set of instructions; and
at least one processor configured to communicate with the storage device, wherein when executing the set of instructions, the at least one processor is configured to cause the system to:
obtain a scout image including a target object;
determine a first area and a second area based on the scout image, wherein the second area is located in the first area;
obtain Positron Emission Tomography (PET) data of the first area and first Computed Tomography (CT) data of the second area; and
reconstruct a PET image with respect to the first area based on the PET data and the first CT data.

17. The system of claim 16, the at least one processor is further configured to cause the system to:
determine whether the scout image includes a non-target object; and
determine the first area based on a result of the determination as to whether the scout image includes a non-target object.

18. The system of claim 17, wherein to determine the first area based on the result of the determination as to whether the scout image includes a non-target object, the at least one processor is configured to cause the system to:
according to a result of the determination that the scout image does not include a non-target object, designate a scan area corresponding to the scout image as the first area.

19. A non-transitory computer readable medium comprising executable instructions that, when executed by at least one processor, cause the at least one processor to effectuate a method, the method comprising:
obtaining a scout image including a target object;
determining a first area and a second area based on the scout image, wherein the second area is located in the first area;
obtaining Positron Emission Tomography (PET) data of the first area and first Computed Tomography (CT) data of the second area; and
reconstructing a PET image with respect to the first area based on the PET data and the first CT data.

20. A method implemented on a computing device having at least one processor, the method comprising:
obtaining, by the at least one processor, a scout image including a target object;
determining, by the at least one processor, a first area based on the scout image;
adjusting, by the at least one processor, the first area to the center of a Positron Emission Tomography (PET) scanning field-of-view (FOV);
obtaining, by the at least one processor, PET data and attenuation information of the first area; and
reconstructing, by the at least one processor, a PET image with respect to the first area based on the PET data and the attenuation information.

* * * * *